United States Patent [19]

Reifschneider et al.

[11] Patent Number: 4,558,039

[45] Date of Patent: Dec. 10, 1985

[54] PHOSPHORUS DERIVATIVES OF 2-FLUOROALKYL-5-PYRIMIDINOLS USEFUL AS INSECTICIDES

[75] Inventors: Walter Reifschneider, Walnut Creek, Calif.; Larry L. Larson, Omaha, Nebr.

[73] Assignee: The Dow Chemical Company, Midland, Mich.

[21] Appl. No.: 619,509

[22] Filed: Jun. 11, 1984

Related U.S. Application Data

[63] Continuation of Ser. No. 443,421, Nov. 22, 1982, abandoned.

[51] Int. Cl.[4] .................... A01N 57/16; A01N 57/32; C07D 239/34; C07F 9/65
[52] U.S. Cl. ..................................... 514/86; 544/243; 544/298
[58] Field of Search ..................... 544/243, 298, 295; 424/200; 514/86

[56] References Cited

U.S. PATENT DOCUMENTS

| | | | |
|---|---|---|---|
| 3,205,231 | 9/1965 | Fest | 544/243 |
| 4,014,882 | 3/1977 | Sharpe | 544/243 |
| 4,127,652 | 11/1978 | Maurer et al. | 424/200 |
| 4,382,087 | 5/1983 | Katz et al. | 424/200 |

FOREIGN PATENT DOCUMENTS 0015296  2/1981  Japan ................... 424/200

OTHER PUBLICATIONS

Inoue et al., Chemical Abstracts, vol. 57, 824f–826b (1962).

Primary Examiner—Donald G. Daus
Assistant Examiner—Diana G. Rivers
Attorney, Agent, or Firm—S. Preston Jones; Ronald G. Brookens

[57] ABSTRACT

Phosphorus derivatives of 2-fluoroalkyl-5-pyrimidinols are taught. These compounds possess insecticidal properties and especially both systemic and foliar activity for plants against insect pest.

35 Claims, No Drawings

PHOSPHORUS DERIVATIVES OF 2-FLUOROALKYL-5-PYRIMIDINOLS USEFUL AS INSECTICIDES

CROSS-REFERENCE TO RELATED APPLICATION

This is a continuation of application Ser. No. 443,421 filed 11.22.82 now abandoned.

BACKGROUND OF THE INVENTION

The present invention relates to new phosphorus derivatives of 2-fluoroalkyl-5-pyrimidinols which possess insecticidal properties and especially both systemic and foliar activity for plants against insect pests. The present invention is also directed to the preparation of said derivatives, active insecticidal compositions containing said derivatives and to the use of such compositions for the kill and control of said pests.

SUMMARY OF THE INVENTION

The present invention is directed to phosphorus derivatives of 5-pyrimidinols which correspond to the formula

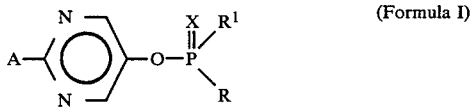
(Formula I)

wherein
A represents fluoroalkyl;
X represents oxygen or sulfur;
R represents alkoxy; and
$R^1$ represents alkyl, alkoxy, alkylthio, monoalkylamino, or phenyl.

These above compounds have been found to have good pesticidal properties especially insecticidal, miticidal, acaricidal and nematicidal properties. The compounds also have systemic activity in plants and foliar activity on plants against attack by said pests.

In the present specification and claims, the terms "alkyl", "alkoxy" and "monoalkylamino" designate straight or branched chain alkyl or alkoxy groups of 1 to 6 carbon atoms.

The term "fluoroalkyl" as employed designates a straight or branched chain alkyl group of 1 to 4 carbon atoms which is substituted with from 1 fluoro atom up to a perfluoro substitution.

The compounds of the present invention are largely somewhat viscous oils or solids which are rather readily soluble in many common organic solvents and of low solubility in water.

The compounds of the present invention can be prepared by the reaction of substantially equimolar amounts of an appropriate 5-pyrimidinol reactant corresponding to the formula

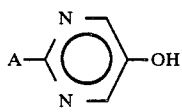

wherein A is as hereinbefore defined, and an appropriate phosphorodichloridate or phosphorochloridothioate corresponding to the formula

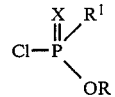

wherein R and $R^1$ are as hereinbefore defined in the presence of a solvent and a hydrogen chloride absorber.

In carrying out the reaction, the reactants are mixed in any suitable fashion and maintained together with agitation until the reaction is complete. It is convenient to first mix the pyrimidinol with the solvent and the HCl acceptor and then add the phosphorus reactant. The reaction is complete when all of the phosphorus reactant has been consumed.

Representative solvents include, for example, acetonitrile, cyclohexane, benzene, toluene, xylene, acetone, methylene chloride, methylethyl ketone, diethylether, dioxane, tetrahydrofuran and the like.

Representative hydrogen chloride absorbers (acid-binding agents) include, for example, alkali metal carbonates such as sodium and potassium carbonates and tertiary amines such as, for example, trimethylamine, triethylamine, pyridine and the like.

At the completion of the reaction, the reaction mixture is filtered to remove any insolubles and the filtrate concentrated under reduced pressure. The residue is then taken up in ethyl ether, benzene, toluene, methylene chloride or chloroform and washed thoroughly with water and then with a saturated sodium chloride solution and dried. The solvent is removed by evaporation under reduced pressure leaving the desired product.

The 2-fluoroalkyl-5-pyrimidinols employed as starting materials can be prepared by the hydrogenation of an appropriate 2-fluoroalkyl-5-(phenylmethoxy)pyrimidine in the presence of a solvent and a hydrogenation catalyst.

In carrying out this reaction, the pyrimidine reactant, the solvent and the catalyst are placed in a hydrogenation vessel. The vessel is purged of all air and hydrogen gas added and the vessel sealed. The hydrogen pressure is from 1 to about 3 or more atmospheres. The temperature employed is from about 0° to about 70° C. It is, however, very convenient to carry out the reaction at room temperature.

After the completion of the reaction, the catalyst is removed by filtration and the filtrate concentrated by evaporation under reduced pressure. The solid, i.e., crude product which forms is then purified by recrystallization from a solvent mixture such as methylene chloride-hexane, or ether-hexane. The desired product is recovered by filtration.

This reaction can be characterized as follows:

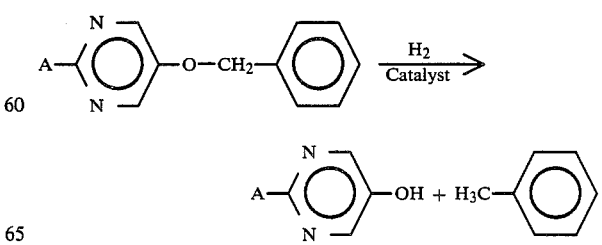

wherein A is as hereinabove set forth. No attempt has been made to present a balanced equation.

The 2-fluoroalkyl-5-(phenylmethoxy)pyrimidine employed as a starting material can be prepared by the reaction of a fluoroalkyl substituted methanimidamide corresponding to the formula

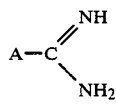

wherein A is as hereinbefore defined, with an about equimolar amount of N-(2-benzyloxy-3-(dimethylamino)-2-propenylidene)-N-methylmethanaminium perchlorate which corresponds to the formula

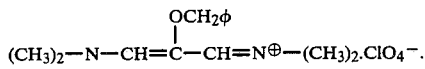

while the perchlorate is exemplified, other salts such as the chloride, or tetrafluoroborate could be employed.

In carrying out the reaction, the reactants are mixed with a solvent such as methanol. To this mixture is slowly added a sodium methoxide solution which had been prepared by the reaction of sodium metal with methanol. After the addition is complete, the mixture is heated under reflux for from about one half to about 4 hours or more depending upon the reactants employed. The mixture is concentrated under reduced pressure and the residue triturated with water. The product is recovered by filtration and washed with water, air dried and recrystallized from a solvent such as isopropanol, hexane, cyclohexane or methylcyclohexane.

The fluoroalkyl substituted methanimidamides can be prepared by the process taught by Reilly et al, J. Chem. Soc. 78, 6032-4 (1956) or by process analogous thereto.

Description of Some Preferred Embodiments

The following examples illustrate the present invention and the manner by which it can be practiced but, as such, should not be construed as limitations upon the overall scope of the same.

EXAMPLE I

O,O-Diethyl O-(2-(trifluoromethyl)-5-pyrimidinyl)-phosphorothioate

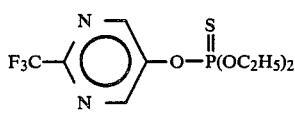

A mixture of 5.0 grams (g) of 2-(trifluoromethyl)-5-pyrimidinol, 6.0 g of finely powdered potassium carbonate, 40 milliliters (ml) of acetonitrile and 5.75 g of O,O-diethyl phosphorochloridothioate was stirred. The temperature rose to 45° C. immediately. After 10 minutes, no more of the starting phosphorus compound could be detected by gas-liquid chromatography (glc). The salts were removed by filtration and the filtrate was concentrated under reduced pressure. The residue was taken up in ether. The ether solution was washed twice with 2% aqueous sodium hydroxide solution, once with saturated sodium chloride solution and dried over anhydrous sodium sulfate. The ether was removed in a rotary evaporator leaving 8.1 g (84 percent of theoretical) of the above-indicated product as a colorless oil having a refractive index of n25/d=1.4607. The infrared (IR) and nuclear magnetic resonance (NMR) spectra were consistent with the desired structure. Upon analysis, the product was found to have carbon, hydrogen and nitrogen contents of 34.36, 3.85 and 8.56 percent, respectively, as compared with the theoretical contents of 34.18, 3.83 and 8.86 percent, respectively, as calculated for the above-named structure (Compound 1).

EXAMPLE II

O,O-Diethyl O-(2-(n-heptafluoropropyl)-5-pyrimidinyl)phosphorothioate

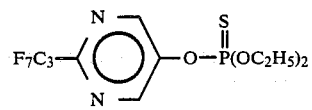

A mixture of 3.96 g of 2-(n-heptafluoropropyl)-5-pyrimidinol, 2.5 g of finely powdered potassium carbonate, 20 ml of acetonitrile and 2.64 g of O,O-diethyl phosphorochloridothioate was stirred for ~45 minutes. By this time, no more of the starting phosphorus compound could be detected by glc. The salts were removed by filtration and the filtrate was concentrated under reduced pressure. The residue was taken up in ether. The ether solution was washed twice with 2% aqueous sodium hydroxide solution, once with saturated sodium chloride solution and dried over anhydrous sodium sulfate. The ether was removed in a rotary evaporator leaving 5.1 g (87.9 percent of theoretical) of the above-indicated product as a colorless oil having a refractive index of n25/d=1.4295. The IR and NMR spectra were consistent with the desired structure. Upon analysis, the product was found to have carbon, hydrogen and nitrogen contents of 31.15, 3.00 and 6.81 percent, respectively, as compared with the theoretical contents of 31.74, 2.91 and 6.73 percent, respectively, as calculated for the above-named structure (Compound 2).

EXAMPLE III

O-Ethyl S-n-propyl O-(2-(n-heptafluoropropyl)-5-pyrimidinyl)phosphorothioate

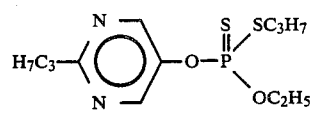

A mixture of 3.96 g of pyrimidinol, 2.5 g of finely powdered potassium carbonate, 20 ml of acetonitrile and 3.06 g of O-ethyl S-n-propyl phosphorochloridothioate was stirred for ~60 minutes. At this time, no more of the starting phosphorus compound could be detected by glc. The salts were removed by filtration and the filtrate was concentrated under reduced pressure. The residue was taken up in ether. The ether solution was washed twice with 2% aqueous sodium hydroxide solution, once with saturated sodium chloride solution and dried over anhydrous sodium sulfate. The ether was removed in a rotary evaporator leaving 4.4 g (70.9 percent of theoretical) of the above-indicated product as a colorless oil having a refractive index of n25/d=1.4619. The IR and NMR spectra were consistent with the desired structure. Upon analysis, the product was found to have carbon, hydrogen and nitrogen contents of 32.51, 3.12 and 6.60 percent, respectively, as compared with the theoretical contents of 32.29, 3.16 and 6.28 percent, respectively, as calculated for the above-named structure (Compound 3).

EXAMPLE IV

O,O-Dimethyl O-(2-(pentafluoroethyl)-5-pyrimidinyl)phosphorothioate

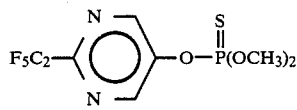

A mixture of 3.21 g of 2-(pentafluoroethyl)-5-pyrimidinol, 2.5 g of finely powdered potassium carbonate, 20 ml of acetonitrile and 2.24 g of O,O-dimethyl phosphorochloridothioate was stirred for ~60 minutes. At this time no more of the starting phosphorus compound could be detected by glc. The salts were removed by filtration and the filtrate was concentrated under reduced pressure. The residue was taken up in ether. The ether solution was washed twice with 2% aqueous sodium hydroxide solution, once with saturated sodium chloride solution and dried over anhydrous sodium sulfate. The ether was removed in a rotary evaporator leaving 4.3 g (91 percent of theoretical) of the above-indicated product as a pale amber colored oil having a refractive index of n25/d=1.4411. The IR and NMR spectra were consistent with the desired structure. Upon analysis, the product was found to have carbon, hydrogen and nitrogen contents of 30.21, 2.53 and 8.75 percent, respectively, as compared with the theoretical contents of 28.41, 2.38 and 8.29 percent, respectively, as calculated for the above-named structure (Compound 4).

EXAMPLE V

N-(1-Methylethyl) O-ethyl O-(2-(trifluoromethyl)-5-pyrimidinyl)phosphoramidothioate

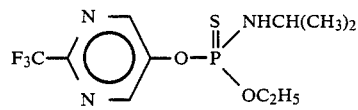

A mixture of 4.9 g of 2-(trifluoromethyl)-5-pyrimidinol, 5.0 g of finely powdered potassium carbonate, 40 ml of acetonitrile and 5.64 g of N-(1-methylethyl) O-ethyl phosphoramidochloridothioate was stirred and heated under reflux for one hour. At this time, no more of the starting phosphorus compound could be detected by glc. The salts were removed by filtration and the filtrate was concentrated under reduced pressure. The residue was taken up in ether. The ether solution was washed twice with 2% aqueous sodium hydroxide solution, once with saturated sodium chloride solution and dried over anhydrous sodium sulfate. The ether was removed in a rotary evaporator leaving 7.2 g (78 percent of theoretical) of the above-indicated product as a colorless oil having a refractive index of n25/d=1.4774. The IR and NMR spectra were consistent with the desired structure. Upon analysis, the product was found to have carbon, hydrogen and nitrogen contents of 36.94, 4.31 and 12.50 percent, respectively, as compared with the theoretical contents of 36.47, 4.59 and 12.76 percent, respectively, as calculated for the above-named structure (Compound 5).

By following the preparative procedures as outlined in the above methods of preparation and the above examples and employing the appropriate starting materials, the following compounds set forth below in Table 1 are prepared.

TABLE 1

| Compound Number | A | X | R | $R^1$ | Refractive Index $n\frac{25}{d} =$ |
|---|---|---|---|---|---|
| 6 | —CF$_3$ | O | —OCH$_3$ | —CH$_3$ | |
| 7 | —CF$_3$ | S | —OCH$_3$ | —OCH$_3$ | 1.4679 |
| 8 | —C$_2$F$_5$ | S | —OC$_2$H$_5$ | —OC$_2$H$_5$ | 1.4449 |
| 9 | —CF$_3$ | O | —OC$_5$H$_{11}$ | —OC$_2$H$_5$ | |
| 10 | —CF$_3$ | S | —OC$_3$H$_7$ | —SC$_2$H$_5$ | 1.5025 |
| 11 | —CF$_3$ | O | —OCH$_3$ | —NHC$_6$H$_{13}$ | |
| 12 | —C$_2$H$_2$F$_3$ | O | —OC$_6$H$_{13}$ | —SC$_6$H$_{13}$ | |
| 13 | —C$_2$H$_2$F$_3$ | S | —OC$_6$H$_{13}$ | —SC$_6$H$_{13}$ | |
| 14 | —C$_3$H$_7$ | S | —OC$_2$H$_5$ | —NHCH(CH$_3$)$_2$ | 1.4385 |
| 15 | —C$_4$F$_9$ | S | —OC$_4$H$_9$ | —OC$_4$H$_9$ | |
| 16 | —C$_2$F$_5$ | S | —OC$_3$H$_7$ | —SC$_2$H$_5$ | 1.4803 |
| 17 | —C$_4$HF$_8$ | S | —OC$_2$H$_5$ | —OC$_2$H$_5$ | |
| 18 | —C$_4$F$_9$ | O | —OC$_6$H$_{13}$ | —OC$_6$H$_{13}$ | |
| 19 | —CF$_3$ | S | —OC$_2$H$_5$ | —φ | 1.5293 |
| 20 | —C$_2$F$_5$ | O | —OCH$_3$ | —C$_6$H$_{13}$ | |
| 21 | —CF$_3$ | O | —OC$_2$H$_5$ | —OC$_2$H$_5$ | 1.4300 |
| 22 | —C$_2$F$_5$ | S | —OC$_2$H$_5$ | —NHCH(CH$_3$)$_2$ | 1.4510 |
| 23 | —CHF$_2$ | S | —OCH$_3$ | —OCH$_3$ | |

EXAMPLE VI 5-(Phenylmethoxy)-2-(trifluoromethyl)pyrimidine

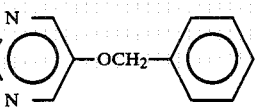

A mixture of 15 g of 2,2,2-trifluoroethanimidamide (Reilly et al, J. Chem. Soc. 78, 6032–4 (1956)), 44 g of N-(2-phenylmethoxy-3-(dimethylamino)-2-propenylidene)-N-methylmethanaminium perchlorate (Holy et al, Collect. Czech. Chem. Commun. 38, 1371–80 (1973)) and 50 ml of methanol was stirred and a sodium methoxide solution, prepared from 6.5 g of sodium metal and 150 ml of methanol, was added dropwise. After the addition was complete, the mixture was heated under reflux for 2.5 hours and was then concentrated under vacuum. The residue which remained was triturated with water and the above-indicated product separated out as a white solid and was recovered by filtration. The product was washed with water, air dried and recrystallized from hexane. The product was recovered as white crystals in a yield of 22.5 g (67 percent of theoretical and melted at 62°–64° C. Upon analysis, the product was found to have carbon, hydrogen and nitrogen contents of 56.83, 3.69 and 10.94 percent, respectively, as compared with the theoretical contents of 56.69, 3.57 and 11.02 percent, respectively, as calculated for the above-named structure.

By following the preparative procedures as outlined above and in the above example and employing the appropriate starting materials, the following compounds set forth below in Table 2 are prepared.

TABLE 2

A—[pyrimidine ring with N's]—OCH$_2$—[phenyl]

| A | Melting point |
|---|---|
| —CHF$_2$ | |
| —C$_2$H$_2$F$_3$ | |
| —C$_2$F$_5$ | 108°–109° C. |
| —C$_3$F$_7$ | 102°–103° C. |
| —C$_4$F$_9$ | |
| —C$_4$HF$_8$ | |

EXAMPLE VII 2-(Trifluoromethyl)-5-pyrimidinol

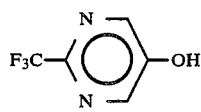

A solution of 8.3 g of 5-(phenylmethoxy)-2-(trifluoromethyl)pyrimidine in 85 ml of absolute ethanol was placed in a Parr hydrogenator along with 0.2 g of 5% palladinum on charcoal and hydrogenated at room temperature and at 40 psi. After hydrogen uptake ceased, the catalyst was removed by filtration and the filtrate concentrated under vacuum. The solid which remained was recrystallized from an ether-hexane mixture and the product was recovered by filtration as white crystals in a yield of 4.7 g (88 percent of theoretical). The product melted at 180°–181.5° C. and upon analysis it was found to have carbon, hydrogen and nitrogen contents of 36.45, 1.95 and 17.28 percent, respectively, as compared with the theoretical contents of 36.60, 1.84 and 17.08 percent, respectively, as calculated for the above-named structure.

By following the preparative procedures as outlined above and in the above example and employing the appropriate starting materials, the following compounds set forth below in Table 3 are prepared.

TABLE 3

A—[pyrimidine ring with N's]—OH

| A | Melting point |
|---|---|
| —CHF$_2$ | |
| —C$_2$H$_2$F$_3$ | |
| —C$_2$F$_5$ | 147.5°–149° C. |
| —C$_3$F$_7$ | 96°–98° C. |
| —C$_4$F$_9$ | |
| —C$_4$HF$_8$ | |

The phosphorochloridate and phosphorochloridothioate reactants are all well known compounds which can be obtained commercially.

The compounds of the present invention are very effective for the kill and control of insects found on the roots or aerial portions of growing plants.

Representative of the various insects which are killed and controlled by the active compounds of the present invention include the mites (Acarina) in particular, the spider mites (Tetranychidae) such as the two-spotted spider mite (*Tetranychus urticae*), carmine spider mite (*Tetranychus cinnabarinus*) and the European red mite (*Panonychus ulmi*), blister mites, for example, the currant blister mite (*Eriophyes ribis*) and tarsonemids, for example, the broad mite (*Hemitarsonemus latus*), the cyclamen mite (*Tarsonemus pallidus*); leafhoppers and planthoppers, i.e., aster leafhopper (*Macrosteles fascifrons*), rice green leafhopper (*Nephotettix virescens*), zig-zag leafhopper (*Recilia dorsalis*), (*Nephotettix apicalis*), white-black planthopper (*Sogattella furcifera*), brown planthopper (*Nilaparvata lugens*), smaller brown planthopper (*Laodelphax striatellus*), grape leafhopper (Erythroneura sp) and potatao leafhopper (*Empoasca fabae*); for insects such as aphids (Aphididae) such as the green peach aphid (*Myzus persicae*), the bean aphid (*Aphis fabae*), the black cherry aphid (*Myzus ceraci*), the pea aphid (*Acythorsiphum pisum*) and the potato aphid (*Macrosiphum euphorbiae*), the currant gall aphid (*Cryptomyzus ribis*), the mealy apple aphid (*Sappaphis mali*), the mealy plum aphid (*Hyalopterus pruni*), the cotton aphid (*Aphis gossyppii*); and other such insects including tobacco budworm (*Heliothis virescens*), Western spotted cucumber beetle (*Diabrotica undecimpunctata undecimpunctata*), housefly (*Musea domestica*), beet armyworm (*Spodoptera exigua*), and codling moth (*Laspeyresica pomonella*).

In the present specification and claims, the term "systemic" defines the translocation of the active compound employed in the present method through the plant. The active compound can be applied either to the aboveground or preferably to below-ground portions of the plant.

The application of an insecticidally effective amount of an active compound of the present invention is critical to the method of the present invention. The active compound can sometimes be employed in unmodified form. Frequently, however, for easier application, the compound is modified by the employment with it of an adjuvant or inert carrier therefor. The practical employment of the beneficial utilities of the present compounds often require that the compounds be composited with one or more adjuvant substances which are chemically inert to the active compound, and the resulting compositions are comprehended within the present invention.

The compositions can be formulated in various forms, such as emulsifiable concentrates, wettable powders, flowable suspension dusts, granules, microencapsulated granules, fine granules, oil sprays, aerosols, and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the active compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising one or more of the presently claimed compounds, an organic liquid as a solvent and carrier therefor, and a propellant material. Numerous other embodiments will become available to those skilled in the art in view of the teachings set forth hereinbelow.

The exact concentration of the active compound in a composition thereof with an adjuvant therefor can vary; it is only necessary that the active compounds be present in a sufficient amount so as to make possible the application of an insecticidally effective dosage. Generally, for practical applications, the active compounds can be broadly applied to the plants or to the soil around the roots of the plants or to water, such as in broadcast rice paddy applications in compositions containing from about 0.00001 percent to about 98 percent by weight of the active compound.

In preparation of dust compositions, the product can be compounded with any of the finely divided carrier solids such as prophyllite, diatomaceous earth, gypsum and the like. In such operations, the finely divided carrier is ground or mixed with the active compound, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, the active compound or a dust concentrate composition containing said compound can be incorporated in intimate mixture with surface-active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the active compound can be compounded with a suitable water-immiscible organic liquid and a surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene liquid halohydrocarbons and synthetic organic oils. The surface-active dispersing agents are usually employed in liquid compositions in the amount of from 0.1 to 20 percent by weight of the combined weight of the dispersing agent and active compound.

When operating in accordance with the present invention, the active compound or a composition containing the active compound is applied to the plants or to their habitat in any convenient manner, for example, by means of hand dusters or sprayers. Application to the foliage of the plants is conveniently carrier out with power dusters, boom sprayers and fog sprayers. In such foliar applications, the employed compositions should not contain any appreciable amounts of any phytotoxic diluents. In large scale operations, dusts, or low-volume sprays can be applied from an airplane.

In further embodiments, one of the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from about 1 to about 99 parts of the compound of the present invention with from about 99 to about 1 part of the additional compound(s).

Dosage amounts are generally from 15–1,000 grams (g) preferably from 40–600 g of active compound and most preferably from 125–500 g of active compound per hectare. However, in special cases, it is possible to exceed or reduce the amount and this may sometimes be necessary.

EXAMPLE VIII

Aqueous dispersions were prepared by admixing one of the hereinafter set forth compounds, dissolved in a suitable inert solvent, with a predetermined quantity of water and a predetermined amount of a surfactant to give aqueous dispersions containing varying predetermined amounts of one of the compounds as the sole toxicant. Separate cotton plants were infested with ~50-100 two-spotted spider mites and individual plants were injected at the base of the plants with one of the dispersions. In a like manner, ~50-100 two-spotted spider mites were placed on control plants and the plants were also injected at the base with a solution containing only water and surfactant. The plants were maintained under conditions conducive to the growth of the plants and the mites. After a period of 5 days, the plants were examined to determine the percent kill and control by the active compound. It was found that at a dosage rate of 600 parts of the active compound per million parts of the ultimate dispersion (ppm) each of compounds 3, 4, 15 and 23 gave at least 50 percent kill and control of the two-spotted spider mites.

EXAMPLE IX

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant.

Separate rice plants were dipped into each of the dispersions and permitted to dry.

A plastic cylinder was placed around each of the plants and 10 adult aster leafhoppers were placed into the cylinder which was then capped. In a like manner, 10 adult aster leafhoppers were placed on control plants which had been dipped in a solution containing only water and surfactant. The plants were maintained under conditions conducive to the growth of the plants and leafhoppers. After a period of three days, the cylinder and plants were examined to determine the concentration in parts of the active compound per million parts of the ultimate dispersion necessary to give 100 percent kill and control of the aster leafhopper. It was found that at a dosage rate of 25 ppm each of compounds 1, 2, 5, 8 and 11 gave 100 percent kill of aster leafhoppers. It was also found that at a dosage rate of 100 ppm, each of compounds 15 and 22 gave 100 percent kill of aster leafhoppers.

EXAMPLE X

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant.

Separate rice plants were treated by adding a predetermined amount of one of the test dispersions to the root of the plant to determine systemic activity.

A plastic cylinder was placed around each of the plants and 10 adult aster leafhoppers were placed in the cylinder and the cylinder capped. In a like manner, 10 adult aster leafhoppers were placed on control plants which were treated at the root zone with a solution containing only water and surfactant. The plants were maintained under conditions conducive to the growth of the plants and leafhoppers. After a period of three days, the cylinder and plants were examined to determine the concentration in parts of the active compound per million parts of the ultimate dispersion necessary to give 100 percent kill and control of the aster leafhopper. It was found that at a dosage rate of 25 parts of the active compound per million parts of the ultimate dispersion (ppm) each of compounds 1, 5, 8, 9 and 17 gave 100 percent kill and control of the aster leafhopper.

EXAMPLE XI

In this operation, aqueous dispersions were prepared by admixing one of the hereinafter set forth compounds, dissolved in a suitable inert solvent, with a predetermined quantity of water and a predetermined amount of a surfactant to give aqueous dispersions of varying predetermined amounts of one of the compounds as the sole active toxicant. Separate 3 inch discs cut from cotton leaves were thoroughly wetted by briefly dipping into one of the dispersions and the wetted leaves were placed in an open petri dish and permitted to dry. After the leaves were dry, 5 live tobacco budworm larvae, 2nd instar, were placed in each petri dish. In identical operations, 5 live tobacco budworm larvae were placed in control petri dishes, the leaf therein having been wetted with a solution containing only water and surfactant. The dishes were maintained at ~80° F. under moist conditions, conducive for the growth of the tobacco budworm larvae, for a period of about 2 days. At the end of the 2-day period, the dishes were examined to determine the minimum concentration in parts of the active compound per million parts of the ultimate dispersion necessary to give at least a 100 percent kill and control of the tobacco budworm larvae. It was found that at a dosage rate of 600 parts of the active compound per million parts of the ultimate dispersion (ppm) each of compounds, 5, 8, 11, 15, 20 and 23 gave 100 percent kill and control of tobacco budworm larvae.

EXAMPLE XII

Seventy-five grams of air-dried soil were placed in an 8-ounce container. To the soil was added sufficient volume of a dispersion, prepared by admixing a predetermined amount of one of the hereinafter set forth compounds with dissolved in a suitable inert solvent, with a predetermined amount of water and a predetermined amount of surfactant, to give various predetermned concentrations of the toxicant in the soil on a soil-chemical basis. The treated soil was air-dried and thoroughly mixed. To each treated container, and control containers treated with water and surfactant alone, was added 0.5 milliliters of an aqueous suspension of the eggs of the Western spotted cucumber beetle (WSCB) (70-80 eggs of 3-4 days old). Additional treated soil was used to cover the eggs and a corn seed was placed in the soil and covered with additional treated soil. The containers were thereafter maintained under conditions conducive to the growth of the seeds and the hatching of the eggs. Ten to twelve (10-12) days after treatment, the containers and the plants therein were examined and it was found that compounds 1, 2, 4, 5, 9, 11, 17 and 23 gave a 100 percent kill and control of the larvae from the hatched eggs at a dosage of 1.5 ppm; compounds 3, 8 and 15 each gave a 100 percent kill and control of the larvae from the hatched eggs at a dosage of 6.2 ppm and compounds 20 and 22 each gave a 100 percent kill and control of the larvae from the hatched egg at a dosage of 25 ppm.

EXAMPLE XIII

In this operation, aqueous dispersions were prepared by admixing one of the hereinafter set forth compounds, dissolved in a suitable inert solvent, with a predetermined quantity of water and a predetermined amount of a surfactant to give aqueous dispersions containing varying predetermined amounts of one of the compounds as the sole active toxicant. Separate cotton plant leaves were thoroughly wetted by briefly dipping into one of the dispersions and the wetted leaves placed in an open petri dish and permitted to dry. After the leaves were dry, 5 live beet armyworm larvae, approximately late 2nd instar were placed in each petri dish. In identical operations, 5 live late 2nd instar beet armyworm larvae were placed in control petri dishes, the leaf therein having been wetted with a solution containing only water and surfactant. The dishes were maintained under moist conditions conducive for the growth of the beet armyworm larvae for a period of about 5 days. At the end of the 5-day period, the dishes were examined to determine the concentration in parts of the active compound per million parts of the ultimate dispersion necessary to give at least a 100 percent kill and control of the beet armyworm larvae. It was found that at a dosage rate of 600 parts of the active compound per million parts of the ultimate dispersion (ppm) each of compounds 5, 8, 11, 20 and 23 gave 100 percent kill and control of beet armyworm larvae. It was also found that each of compounds 2, 9, 15 and 17 gave 100 percent kill and control of beet armyworm larvae.

What is claimed is:

1. A compound corresponding to the formula 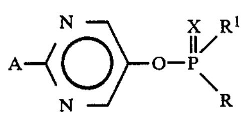 wherein

A represents perfluoroalkyl;

X represents oxygen or sulfur;

R represents alkoxy; and $R^1$ represents alkyl, alkoxy, alkylthio, monoalkylamino or phenyl.

2. A compound as defined in claim 1 wherein A is $-CF_3$.

3. The compound as defined in claim 2 which is O,O-diethyl O-(2-(trifluoromethyl)-5-pyrimidinyl)phosphorothioate.

4. The compound as defined in claim 2 which is N-(1-methylethyl) O-ethyl O-(2-(trifluoromethyl)-5-pyrimidinyl)phosphoramidothioate.

5. A compound as defined in claim 1 wherein A is $-C_2F_5$.

6. The compound as defined in claim 5 which is O,O-diethyl O-(2-(pentafluoroethyl)-5-pyrimidinyl)phosphorothioate.

7. The compound as defined in claim 5 which is O-ethyl S-propyl O-(2-(pentafluoroethyl)-5-pyrimidinyl)-phosphorodithioate.

8. A compound as defined in claim 1 wherein A is $-C_3F_7$.

9. The compound as defined in claim 8 which is O,O-diethyl O-(2-(n-heptofluoropropyl)-5-pyrimidinyl)phosphorothioate.

10. An insecticidal composition comprising an inert carrier in intimate admixture with an insecticidally effective amount of an active compound corresponding to the formula wherein A represents perfluoroalkyl;

X represents oxygen or sulfur;

R represents alkoxy; and $R^1$ represents alkyl, alkoxy, alkylthio, monoalkylamino or phenyl.

11. A composition as defined in claim 10 wherein A is $-CF_3$.

12. The composition as defined in claim 11 wherein the active compound is O,O-diethyl O-(2-(trifluoromethyl)-5-pyrimidinyl)phosphorothioate.

13. The composition as defined in claim 11 wherein the active compound is N-(1-methylethyl)O-ethyl O-(2-(trifluoromethyl)-5-pyrimidinyl)phosphoramidothioate.

14. A composition as defined in claim 10 wherein A is $-C_2F_5$.

15. The composition as defined in claim 14 wherein the active compound is O,O-diethyl-O-(2-(pentafluoroethyl)-5-pyrimmidinyl)phosphorothioate.

16. The composition as defined in claim 14 wherein the active compound is O-ethyl S-propyl O-(2-(pentafluoroethyl)-5-pyrimidinyl)phosphorodithioate.

17. A composition as defined in claim 10 wherein A is $-C_3F_7$.

18. The composition as defined in claim 17 wherein the active compound is O,O-diethyl O-(2-(n-heptofluoropropyl)-5-pyrimidinyl)phosphorothioate.

19. A method for the kill and control of insects which comprises contacting said insects or their habitat with a composition comprising an inert carrier in intimate admixture with an insecticidally effective amount of an active compound corresponding to the formula wherein A represents perfluoroalkyl;

X represents oxygen or sulfur;

R represents alkoxy; and $R^1$ represents alkyl, alkoxy, alkylthio, monoalkylamino or phenyl.

20. A method as defined in claim 19 wherein A is $-CF_3$.

21. The method as defined in claim 20 wherein the active compound is O,O-diethyl O-(2-(trifluoromethyl)-5-pyrimidinyl)phosphorothioate.

22. The method as defined in claim 20 wherein the active compound is N-(1-methylethyl)O-ethyl O-(2-(trifluoromethyl)-5-pyrimidinyl)phosphoramidothioate.

23. A method as defined in claim 19 wherein a is $-C_2F_5$.

24. The method as defined in claim 23 wherein the active compound is O,O-diethyl O-(2-(pentafluoroethyl)-5-pyrimidinyl)phosphorothioate.

25. The method as defined in claim 23 wherein the active compound is O-ethyl S-propyl O-(2-(pentafluorethyl)-5-pyrimidinyl)phosphorodithioate.

26. A method as defined in claim 19 wherein A is —C₃F₇.

27. The method as defined in claim 26 wherein the active compound is O,O-diethyl O-(2-(n-heptofluoropropyl)-5-pyrimidinyl)phosphorothioate.

28. A compound corresponding to the formula

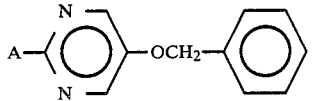

wherein
A is perfluoroalkyl.

29. The compound as defined in claim 28 which is 2-(trifluoromethyl)-5-(phenylmethoxy)pyrimidine.

30. The compound as defined in claim 28 which is 2-(pentafluoroethyl)-5-(phenylmethoxy)pyrimidine.

31. The compound as defined in claim 28 which is 2-(heptafluoropropyl)-5-(phenylmethoxy)pyrimidine.

32. A compound corresponding to the formula

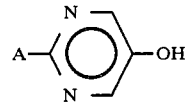

wherein
A is perfluoroalkyl.

33. The compound as defined in claim 32 which is 2-(trifluoromethyl)-5-pyrimidinol.

34. The compound as defined in claim 32 which is 2-(pentafluoroethyl)-5-pyrimidinol.

35. The compound as defined in claim 32 which is 2-(heptafluoropropyl)-5-pyrimidinol.

* * * * *